United States Patent [19]

Hirschberg et al.

[11] Patent Number: 5,314,452
[45] Date of Patent: May 24, 1994

[54] PROTECTIVE ARRANGEMENT FOR AN IMPLANTABLE DEFIBRILLATOR

[75] Inventors: Jakub Hirschberg, Taeby; Hans Strandberg, Sundbyberg, both of Sweden

[73] Assignee: Siemens Aktiengesellschaft, Munich, Fed. Rep. of Germany

[21] Appl. No.: 946,599

[22] Filed: Sep. 18, 1992

[30] Foreign Application Priority Data

Sep. 23, 1991 [EP] European Pat. Off. ............ 91116160

[51] Int. Cl.⁵ .............................................. A61N 1/08
[52] U.S. Cl. ..................................... 607/36; 607/63; 607/37; 128/908
[58] Field of Search ............... 128/419 D, 908, 419 P, 128/419 PT, 419 R; 607/36, 37, 2, 63, 34

[56] References Cited

U.S. PATENT DOCUMENTS

| | | | |
|---|---|---|---|
| 3,508,538 | 4/1970 | Keller, Jr. ........... | 128/419 PT |
| 3,625,201 | 12/1971 | Murphy, Jr. .......... | 128/419 PT |
| 3,798,542 | 4/1974 | Dempsey ............. | 128/419 D |
| 3,983,476 | 9/1976 | Konopasek .......... | 128/419 D |
| 4,830,005 | 5/1989 | Woskow .............. | 128/419 PT |

FOREIGN PATENT DOCUMENTS

| | | | |
|---|---|---|---|
| 0315368 | 5/1989 | European Pat. Off. . | |
| 3701473 | 7/1987 | Fed. Rep. of Germany | 128/908 |
| 2053539 | 4/1971 | France . | |
| 1267046 | 3/1972 | United Kingdom | 607/9 |

Primary Examiner—William E. Kamm
Assistant Examiner—Kennedy J. Schaetzle
Attorney, Agent, or Firm—Hill, Steadman & Simpson

[57] ABSTRACT

In order to prevent a person handling a defibrillator during manufacture and in conjunction with implantation of the defibrillator from receiving an electrical shock due to a fault, a protective arrangement is provided for the defibrillator. This protective arrangement is in the form of a plug part detachably connectable to the defibrillator housing and having terminal pins engaging into the connecting sockets of the defibrillator which is present for receiving the electrode leads. The terminal pins produce an electrically conductive connection in the sockets and are directly connected to one another inside the plug part via an electrical resistor. In case of a fault, the high-voltage energy generated between the connecting sockets is harmlessly absorbed in the resistor.

4 Claims, 1 Drawing Sheet

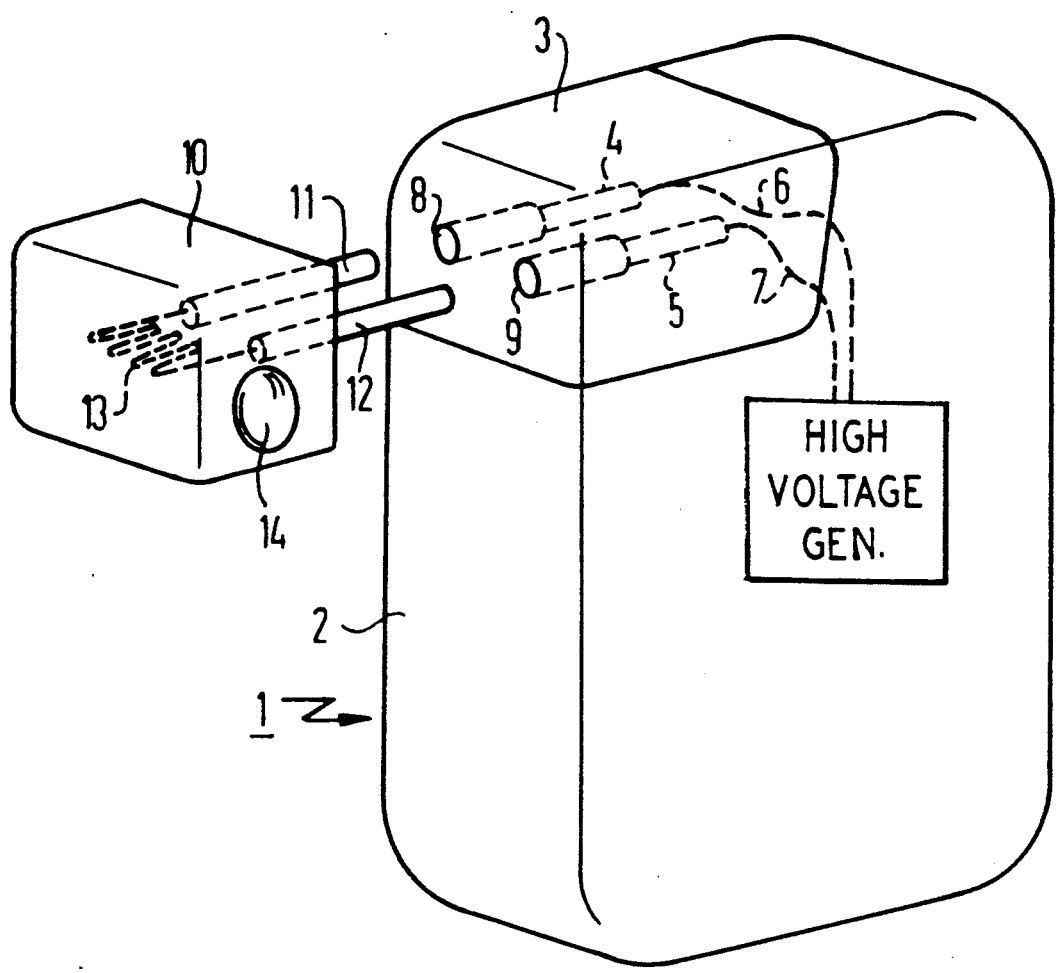

PROTECTIVE ARRANGEMENT FOR AN IMPLANTABLE DEFIBRILLATOR

BACKGROUND OF THE INVENTION

1. Field of the Invention

The present invention is directed to a protective arrangement for an implantable defibrillator of the type having jacks or sockets for the electrical and mechanical connection of electrode leads to the housing.

2. Description of the Prior Art

As is known, implantable defibrillators contain a high-voltage generator arranged in the housing of the defibrillator, which generates a high-voltage pulse at the connecting jacks or sockets on demand. This pulse is then delivered to the heart to be defibrillated via lead terminating electrodes disposed at or in the proximity of the heart. The demand for delivering a high-voltage output pulse can ensue automatically after evaluating mensurationally acquired physiological parameters that indicate a fibrillation condition of the heart or can ensue proceeding extracorporeally outside via a programming device, for example for testing purposes.

In order to prevent a person handling the defibrillator during manufacture, and later in conjunction with the implantation of the defibrillator, from receiving an electrical shock due to some kind of fault, a protective arrangement is disclosed herein for an implantable defibrillator of the type described above which includes a plug part, with terminal pins, that is detachably connectable to the defibrillator housing, these terminal pins being insertable into the connecting sockets while producing an electrically conductive connection and being directly connected to one another via an electrical resistor inside the plug part.

A generally similar plug part for a heart pacemaker is disclosed in U.S. Pat. No. 4,830,005, however, in that known plug a resistor is arranged between the terminal pins in series with a magnetic switch, the magnetic switch being capable of being closed for testing purposes with an external testing magnet. This known plug thus does not represent protection against high-voltage but is instead for simulating the heart impedance using the resistor in order to be able to test the heart pacemaker for functionability before an implantation. A high-voltage protection is not achieved with this known arrangement because the magnetic switch is not opened in the normal case.

An arrangement is disclosed in U.S. Pat. No. 3,998,542 composed of a resistor cascade with a glow lamp as a display element for testing the output energy of defibrillators. This known test circuit has contact surfaces against which the electrodes of the defibrillator are planarly applied in order to subsequently trigger the output of a high-voltage pulse by the defibrillator. Again, no high-voltage protection whatsoever is provided.

SUMMARY OF THE INVENTION

It is an object of the present invention to provide a protective arrangement for an implantable defibrillator which prevents those handling the defibrillator against electrical shock from the high-voltage components of the defibrillator.

As noted above, this object is achieved in accordance with the principles of the present invention in a plug part which is detachable from the defibrillator housing and which has terminal pins receivable in the sockets used to connect the electrode leads, the terminal pings being electrically connected together within the plug part through a resistor.

Differing from the known test circuits, the protective arrangement of the invention guarantees an effective high-voltage protection, because not only are the connecting sockets of the defibrillator protected against accidental touching, but also the high-voltage energy generated between the connecting sockets is harmlessly absorbed in the resistor even in case of a fault. A further advantage is that a possible short-circuiting of the connecting sockets, and thus damage to the defibrillator due to a high-voltage source, is prevented. In defibrillators that have more than two connecting sockets carrying high-voltage, the resistor is composed of a plurality of individual elements that are arranged between a plurality of terminal pins corresponding to the number of sockets. For connecting the electrodes or when implementing specific tests wherein the connecting sockets that carry the high-voltage must be accessible, the plug part is simply removed from the housing of the defibrillator. Otherwise, however, the defibrillator can be tested with the plug part inserted in the sockets, whereby the resistor serves as a load. This is particularly advantageous when the defibrillator is already packaged in a sterile manner, because the test can be implemented without having to open the packaging.

A reliable absorption of the high-voltage energy output at the connecting sockets in the event of a faulty defibrillator is advantageously achieved by the value of resistance of the resistor being on the order of magnitude of 10Ω.

The plug part is preferably composed of an insulating plastic compound into which the resistor is cast. A reliable protection against accidental contact is guaranteed in this way while still permitting the plug part to be simply manufactured.

In order to be able to easily separate the plug part from the defibrillator when implanting the defibrillator, the plug is preferably provided with lateral gripping depressions.

DESCRIPTION OF THE DRAWINGS

The single FIGURE shows an implantable defibrillator together with an exemplary embodiment of the protective arrangement of the invention provided for the defibrillator.

DESCRIPTION OF THE PREFERRED EMBODIMENTS

The illustrated defibrillator 1 has a metallic housing 2 that is provided with a connector part 3 of plastic for the connection of electrode leads (not shown). Two connecting sockets 4 and 5 extend into the plastic part 3, these connecting sockets 4 and 5 being connected to a high-voltage generator 15 in the inside of the housing 2 via connecting lines 6 and 7. The connecting sockets 4 and 5 are accessible from the exterior through bores 8 and 9 in the plastic part 3.

A plug part 10 has two terminal pins 11 and 12 corresponding in number and position to the connecting sockets 4 and 5 (more than tow sockets and more than two terminal pins may be present). The terminal pins 11 and 12 are connected to one another in the inside of the plug part 10 via a wire resistor 13 having a resistance value on the order of magnitude of 10Ω. The plug part 10 is composed of an insulating plastic compound into which the wire resistor 13 and the end parts of the terminal pins 11 and 12 connected thereto are cast. In order to facilitate the manipulation of the plug part 10 when being plugged onto the housing 2 or when being separated from the housing 2, the plug part 10 is provided with lateral gripping depressions 14.

As long as the defibrillator 1 is not implanted or is connected to electrode lines via the connecting sockets 4 and 5 for testing purposes, the terminal pins 11 and 12 of the plug part 10 are inserted into the connecting sockets 4 and 5. If a high-voltage were then to appear at the connecting sockets 4 and 5 due to a defect in the control and high-voltage circuitry of the defibrillator 1, then the high-voltage energy is absorbed in the resistor 13 in a way that is safe for the person handling the defibrillator 1. The plug part 10, moreover, is only removed from the defibrillator 1 for connecting the electrode leads to the implanted defibrillator 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A protective arrangement for an implantable defibrillator containing high-voltage components, said defibrillator having a housing with exposed sockets for the connection of electrode leads to said high-voltage components, said protective arrangement consisting of a non-conductive plug part detachably connectable to said defibrillator housing, said plug part having two terminal pins insertable into said sockets with said plug part completely covering said sockets, and an electrical resistor directly connected between said terminal pins, said terminals and forming means for producing a constant electrically conductive path between said sockets and protecting against discharge of said high-voltage components.

2. A protective arrangement as claimed in claim 1, wherein said resistor has a resistance value of approximately 10Ω.

3. A protective arrangement as claimed in claim 1, wherein said plug part is composed of an insulating plastic compound into which the resistor is cast.

4. A protective arrangement as claimed in claim 1, wherein said plug part has lateral gripping depressions.

* * * * *